United States Patent [19]

Chen

[11] Patent Number: 5,840,929
[45] Date of Patent: Nov. 24, 1998

[54] C4 METHOXY ETHER DERIVATIVES OF PACLITAXEL

[75] Inventor: Shu-Hui Chen, Hamden, Conn.

[73] Assignee: Bristol-Myers Squibb Company, Princeton, N.J.

[21] Appl. No.: 709,673

[22] Filed: Sep. 9, 1996

Related U.S. Application Data

[63] Continuation of Ser. No. 422,374, Apr. 14, 1995, abandoned.

[51] Int. Cl.$^6$ .................................................. C07D 305/14
[52] U.S. Cl. ........................................... 549/510; 549/511
[58] Field of Search ..................... 549/510, 511

[56] References Cited

U.S. PATENT DOCUMENTS

| | | | |
|---|---|---|---|
| 4,814,470 | 3/1989 | Colin et al. | 514/449 |
| 4,960,790 | 10/1990 | Stella et al. | 514/449 |
| 5,254,580 | 10/1993 | Chen et al. | 514/449 |
| 5,272,171 | 12/1993 | Ueda et al. | 514/449 |
| 5,294,637 | 3/1994 | Chen et al. | 514/449 |
| 5,395,850 | 3/1995 | Roth | 514/471 |

FOREIGN PATENT DOCUMENTS

| | | |
|---|---|---|
| 590267A2 | 4/1994 | European Pat. Off. . |
| 600517A1 | 6/1994 | European Pat. Off. . |
| 604910A1 | 7/1994 | European Pat. Off. . |
| WO93/06093 | 4/1993 | WIPO . |
| WO94/14787 | 7/1994 | WIPO . |

OTHER PUBLICATIONS

E. K. Rowinsky and R.C. Donehower, "The Clinical Pharmacology and Use of Antimicrotubule Agents in Cancer Chemotherapeutics," Pharmac. Ther., 52:35–84, 1991.

C. M. Spencer and D. Faulds, "Paclitaxel, A Review of its Pharmacodynamic and Pharmacokinetic Properties and Therapeutic Potential in the Treatment of Cancer," DRUGS, 48(5), 794–847, 1994.

K.C. Nicolaou, et al, "Chemistry and Biology of Taxol," Angew. Chem., Int. Ed. Engl., 33:15–44, 1994.

Greene and Wuts, Protective Groups in Organic Synthesis, 2nd Ed., John Wiley & Sons, and McOmie, 1991.

Protective Groups in Organic Chemistry, Ed. J.F.W. McOmie, Plenum Press, 1973.

S.–H. Chen, et al, "First Syntheses of Novel Paclitaxel (Taxol) Analogs Modified at the C4–Position," J. Org. Chem., 59, pp. 6156–6158, 1994.

S.–H. Chen, et al, "Structure–Activity Relationships of Taxol: Synthesis and Biological Evaluation of C2 Taxol Analogs," Bioorganic and Medicinal Chemistry Letters, vol. 4, No. 3, pp. 479–482, 1994.

R.A. Johnson, et al, "Taxol Chemistry. 7–O–Triflates as Precursors to Olefins and Cyclopropanes," Tetrahedron Letters, vol. 35, No. 43, pp. 7893–7896, 1994.

G. Roth, et al, "Reaction of Paclitaxel and 10–Desacetyl Baccatin III with Diethylamino Sulfurtrifluoride," Tetrahedron Letters, vol. 36, No. 10, pp. 1609–1612, 1995.

S.–H. Chen, et al, "The Chemistry of Taxanes: Reaction of Taxol and Baccatin Derivatives with Lewis Acids in Aprotic and Protic Media," Tetrahedron, vol. 49, No. 14, pp. 2805–2828, 1993.

Physician's Desk Reference, 49th Edition, Medical Economics, p. 682, 1995.

J. Kant, et al, "A Chemoselective Approach to Functionalize the C–10 Position of 10–Deacetylbaccatin III. Synthesis and Biological Properties of Novel C–10 Taxel Analogues," Tetrahedron Letters, 35, No. 31, pp. 5543–5546, 1994.

S.–H. Chen, et al, "Taxol® Structure–Activity Relationships: Synthesis and Biological Evaluation of Taxol Analogs Modified at C–7," Bioorganic & Medicinal Chemistry Letters, vol. 4, No. 18, pp. 2223–2228, 1994.

Mahendra D. Chordia, et al, "Synthesis and Biological Evaluation of 4–Deacetoxy–paclitaxel," Tetrahedron Letters, vol. 35, No. 37, pp. 6843–6846, 1994.

D. A. Scudieri, et al, Evaluation of Soluble Tetrazolium/ Formazan Assay for Cell Growth and Drug Sensitivity in Culture Using Human and Other Tumor Cell Lines, Cancer Res., vol. 48, pp. 4827–4833. 1988.

K.A. Neidigh, et al, "Synthesis and Biological Evaluation of 4–Deacetylpaclitaxel," Tetrahedron Letters, vol. 35, No. 37, pp. 6839–6842, 1994.

*Primary Examiner*—Ba K. Trinh
*Attorney, Agent, or Firm*—Samuel J. DuBoff

[57] ABSTRACT

The present invention concerns novel paclitaxel derivatives, their use as antitumor agents, and pharmaceutical formulations.

4 Claims, No Drawings

C4 METHOXY ETHER DERIVATIVES OF PACLITAXEL

This application is a continuation of application Ser. No. 08/422,374 filed Apr. 14, 1995, now abandoned.

BACKGROUND OF THE INVENTION

1. Field of the Invention

The present invention concerns antitumor compounds. More particularly, the invention provides novel paclitaxel derivatives, pharmaceutical formulations thereof, and their use as antitumor agents.

2. Background Art

Taxol® (paclitaxel) is a natural product extracted from the bark of Pacific yew trees, Taxus brevifolia. It has been shown to have excellent antitumor activity in in vivo animal models, and recent studies have elucidated its unique mode of action, which involves abnormal polymerization of tubulin and disruption of mitosis. It has recently been approved for the treatment of refractory advanced ovarian cancer and breast cancer; and studies involving other cancers have shown promising results. The results of paclitaxel clinical studies are reviewed by numerous authors such as by Rowinsky and Donehower in "The Clinical Pharmacology and Use of Antimicrotubule Agents in Cancer Chemotherapeutics," Pharmac. Ther., 52:35–84, 1991; by Spencer and Faulds in "Paclitaxel, A Review of its Pharmacodynamic and Pharmacokinetic Properties and Therapeutic Potential in the Treatment of Cancer," Drugs, 48 (5) 794–847, 1994; and by K. C. Nicolaou et al. in "Chemistry and Biology of Taxol," Angew. Chem., Int. Ed. Engl., 33: 15–44, 1994, and also in the references cited therein.

A semi-synthetic analog of paclitaxel named Taxotere® (docetaxel) has also been found to have good antitumor activity in animal models. Taxotere® is also currently undergoing clinical trials in Europe and in the United States. The structures of paclitaxel and Taxotere® are shown below along with the conventional numbering system for molecules belonging to the class; such numbering system is also employed in this application.

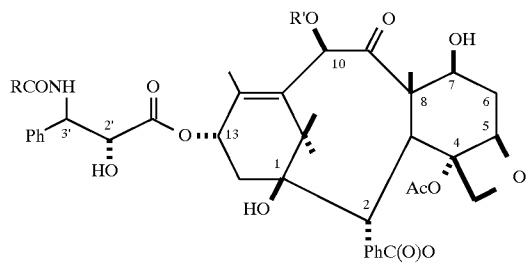

Taxol®: R=Ph; R'=acetyl

Taxotere®: R=t-butoxy; R'=hydrogen

We recently disclosed in PCT patent application WO 94/14787 published Jul. 7, 1994 that C4 esters, carbonates, and carbamates derivatives of paclitaxel are potent antitumor agents. We have now discovered that C4 methoxy derivatives of paclitaxel, heretofore unknown, are also potent antitumor agents.

SUMMARY OF THE INVENTION

This invention relates to novel antitumor compounds represented by formula I

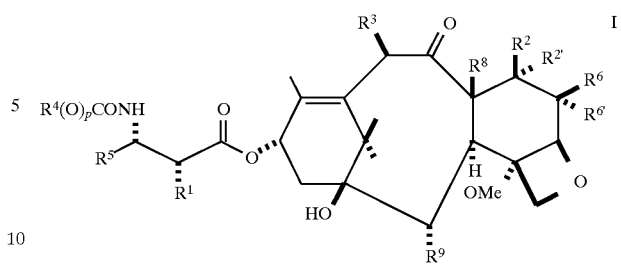

wherein $R^1$ is hydroxy, —OC(O)$R^x$ or —OC(O)O$R^x$; $R^2$ is hydrogen, hydroxy, —OC(O)$R^x$ or —OC(O)O$R^x$; $R^{2'}$ is hydrogen, hydroxy or fluoro; $R^{6'}$ is hydrogen or hydroxy, or $R^{2'}$ and $R^{6'}$ together can form oxirane ring; $R^3$ is hydrogen, $C_{1-6}$ alkyloxy, hydroxy, —OC(O)$R^x$, —OC(O)O$R^x$ or —OCONR$^7$R$^{11}$; $R^8$ is methyl, or $R^8$ and $R^2$ together can form cyclopropane ring; $R^6$ is hydrogen, or $R^6$ and $R^2$ together can constitute a bond; $R^9$ is hydroxy or —OC(O) $R^x$; with the proviso that when $R^8$ and $R^2$ form cyclopropane ring, $R^2$ is hydrogen; when $R^{2'}$ and $R^{6'}$ form oxirane ring, $R^2$ is hydrogen; when $R^2$ and $R^6$ form a double bond, $R^{2'}$ and $R^{6'}$ are hydrogen; when $R^2$ is hydroxy, $R^{2'}$ is hydrogen; when $R^{2'}$ is fluoro, $R^2$ is hydrogen; $R^7$ and $R^{11}$ are independently $C_{1-6}$ alkyl, hydrogen, aryl or substituted aryl; $R^4$ and $R^5$ are independently $C_{1-6}$ alkyl, $C_{2-6}$ alkenyl, $C_{2-6}$ alkynyl, or —Z—$R^{10}$; Z is a direct bond, $C_{1-6}$ alkyl or $C_{2-6}$ alkenyl; $R^{10}$ is aryl, substituted aryl, $C_{3-6}$ cycloalkyl or heteroaryl; p is 0 or 1; $R^x$ is $C_{3-6}$ cycloalkyl, $C_{2-6}$ alkenyl, $C_{1-6}$ alkyl, all can be optionally substituted with one to six same or different halogen atoms or hydroxy; $R^x$ is a radical of the formula

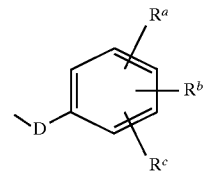

wherein D is a bond or $C_{1-6}$ alkyl; and $R^a$, $R^b$ and $R^c$ are independently hydrogen, amino, $C_{1-6}$ alkylamino, di-$C_{1-6}$ alkylamino, halogen, $C_{1-6}$ alkyl, or $C_{1-6}$ alkoxy.

Another aspect of the present invention provides a method for inhibiting tumor in a mammalian host which comprises administering to said mammalian host an antitumor effective amount of a compound of formula I.

Yet, an other aspect of the present invention provides a pharmaceutical formulation which comprises an antitumor effective amount of a compound of formula I and a pharmaceutically acceptable carrier.

In the application, unless otherwise specified explicitly or in context, the following definitions apply. The numbers in the subscript after the symbol "C" define the number of carbon atoms a particular group can contain. For example "$C_{1-6}$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "$C_{1-6}$ alkyl" can also refer to $C_{1-6}$ alkylene which bridges two groups; examples include propane-1,3-diyl, butane-1,4-diyl, 2-methyl-butane-1, 4-diyl, etc. "$C_{2-6}$ alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_{2-6}$ alkenyl" can also refer to $C_{2-6}$ alkenediyl which bridges two groups; examples include ethylene-1,2-diyl (vinylene), 2-methyl-2-butene-1,4-diyl, 2-hexene-1,6-diyl, etc. "$C_{3-6}$ alkynyl" means a straight or branched carbon chain having at least one carbon-carbon triple bond, and from two to six carbon atoms; examples include ethynyl, propynyl, butynyl, and hexynyl.

"Aryl" means aromatic hydrocarbon having from six to ten carbon atoms; examples include phenyl and naphthyl. "Substituted aryl" means aryl substituted with at least one group selected from $C_{1-6}$ alkanoyloxy, hydroxy, halogen, $C_{1-6}$ alkyl, trifluoromethyl, $C_{1-6}$ alkoxy, aryl, $C_{2-6}$ alkenyl, $C_{1-6}$ alkanoyl, nitro, amino, $C_{1-6}$ alkylamino, di-$C_{1-6}$ alkylamino, and amido. "Halogen" means fluorine, chlorine, bromine, and iodine.

"Heteroaryl" means a five- or six-membered aromatic ring containing at least one and up to four non-carbon atoms selected from oxygen, sulfur and nitrogen. Examples of heteroaryl include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, and like rings.

"Hydroxy protecting groups" include, but is not limited to, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, dialkylsilylethers, such as dimethylsilyl ether, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, benzyl, and p-nitrophenyl. Additional examples of hydroxy protecting groups may be found in standard reference works such as Greene and Wuts, *Protective Groups in Organic Synthesis*, 2d Ed., 1991, John Wiley & Sons, and McOmie; and *Protective Groups in Organic Chemistry*, 1975, Plenum Press. Methods for introducing and removing protecting groups are also found in such textbooks.

The term "taxane" or "taxane core" refers to the framework with the structure:

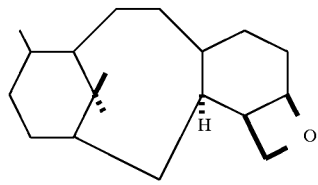

The cycloprane group which can be constituted from $R^8$ and $R^2$ of formula I can alternatively be referred to as "7β,8β-methano" group as in Tetrahedron Letters, Vol 35, No 43, pp 7893–7896 (1994) or as "cyclopropa" group as in U.S. Pat. No. 5,254,580 issued Oct. 19, 1993. When $R^2$ and $R^6$ form a bond, naturally there will be a double bond between C7 and C6.

In compounds of formula I, examples of $R^x$ include methyl, hydroxymethyl, ethyl, n-propyl, isopropyl, n-butyl, isobutyl, chloromethyl, 2,2,2-trichloroethyl, cyclopropyl, cyclobutyl, cyclopentyl, cyclohexyl, ethenyl, 2-propenyl, phenyl, benzyl, bromophenyl, 4-aminophenyl, 4-methylaminophenyl, 4-methylphenyl, 4-methoxyphenyl and the like. Examples of $R^4$ and $R^5$ include 2-propenyl, isobutenyl, 3-furanyl (3-furyl), 3-thienyl, phenyl, naphthyl, 4-hydroxyphenyl, 4-methoxyphenyl, 4-fluorophenyl, 4-trifluoromethylphenyl, methyl, ethyl, n-propyl, isopropyl, n-butyl, isobutyl, t-butyl, ethenyl, 2-propenyl, 2-propynyl, benzyl, phenethyl, phenylethenyl, 3,4-dimethoxyphenyl, 2-furanyl (2-furyl), 2-thienyl, 2 -(2-furanyl)ethenyl, 2-methylpropyl, cyclopropyl, cyclobutyl, cyclopentyl, cyclohexyl, cyclohexylmethyl, cyclohexylethyl and the like.

The new products that have the general formula I display a significant inhibitory effect with regard to abnormal cell proliferation, and have therapeutic properties that make it possible to treat patients who have pathological conditions associated with an abnormal cell proliferation. The pathological conditions include the abnormal cellular proliferation of malignant or non-malignant cells in various tissues and/or organs, including, non-limitatively, muscle, bone and/or conjunctive tissues; the skin, brain, lungs and sexual organs; the lymphatic and/or renal system; mammary cells and/or blood cells; the liver, digestive system, and pancreas; and the thyroid and/or adrenal glands. These pathological conditions can also include psoriasis; solid tumors; ovarian, breast, brain, prostate, colon, stomach, kidney, and/or testicular cancer, Karposi's sarcoma; cholangiocarcinoma; choriocarcinoma; neuroblastoma; Wilm's tumor, Hodgkin's disease; melanomas; multiple myelomas; chronic lymphocytic leukemias; and acute or chronic granulocytic lymphomas. The novel products in accordance with the invention are particularly useful in the treatment of non-Hodgkin's lymphoma, multiple myeloma, melanoma, and ovarian, urothelial, oesophageal, lung, and breast cancers. The products in accordance with the invention can be utilized to prevent or delay the appearance or reappearance, or to treat these pathological conditions.

The compounds of this invention can be made by conventional organic chemistry techniques. Scheme I, which depicts a process that some compounds within the scope of formula I can be made, is shown for illustrative purposes only, and are not to be construed as limiting the methods to make the compounds by any other methods.

All steps in Scheme I are within the routine organic chemistry repertoire and need no elaborate explanation. For example, compound III of Scheme I can be obtained from compound II by the three-step sequence described by Chen et al in *J. Organic Chemistry*, 59, pp. 6156–6158 (1994). The well-known Holton coupling of Process (g) of Scheme I involves the coupling of β-lactams with protected baccatin III derivatives. The background of the Holton process and its improvements can be found, for example, in European patent application No. 604,910 published Jul. 6, 1994.

Compounds of formula I with groups on the taxane core different from paclitaxel can also be readily made by following the well established paclitaxel chemistry. For example as in Scheme II, C2, C6, C7, C10, and/or C8 position can be derivatized by essentially following the published procedure, or obvious variants thereof, into a compound of formula XI in which $R^3$, $R^8$, $R^2$, $R_{2'}$, $R^9$, $R^{6'}$ and $R^6$ have the meanings defined earlier. Subsequently, C4-acetyloxy group in a compound of formula XI can be converted to the methoxy group by a sequence of steps analogous to those in Scheme I. For example, for converting C2-benzoyloxy to other groups see, S. H. Chen et al, *Bioorganic and Medicinal Chemistry Letters*, Vol. 4, No. 3, pp 479–482 (1994); for modifying C10-acetyloxy see, J. Kant et al, *Tetrahedron Letters, Vol.* 35, No. 31, pp 5543–5546 (1994) and U.S. Pat. No. 5,294,637 issued Mar. 15, 1994; for making C10 and/or C7 unsubstituted (deoxy) derivatives see, European Patent Application 590,267A2 published Apr. 6, 1994 and PCT application WO 93/06093 published Apr. 1, 1993; for making 7β,8β-methano, 6,7-α, α-dihydroxy and 6,7-olefinic groups see, R. A. Johnson, Tetrahedron Letters, Vol. 35, No 43, pp 7893–7896 (1994), U.S. Pat. No. 5,254,580, issued Oct. 19, 1993, and European Patent Application 600,517A1 published Jun. 8, 1994; for making C7/C6 oxirane see, U.S. Pat. No. 5,395,850 issued Mar. 7, 1995; for making C7-epi-fluoro see, G. Roth et al, Tetrahedron Letters, Vol 36, pp 1609–1612 (1993); for forming C7 esters and carbonates see, U.S. Pat. No. 5,272,171 issued Dec. 21, 1993 and S. H. Chen et al., Tetrahedron, 49, No. 14, pp 2805–2828 (1993). A compound of formula XII can be converted into a final product, comprising reacting the compound with a β-lactam (the Holton process).

Alternatively C2, C6, C7, C10, and/or C8 position of a compound of formula V is derivatized first and then coupled with a β-lactam, see Scheme III.

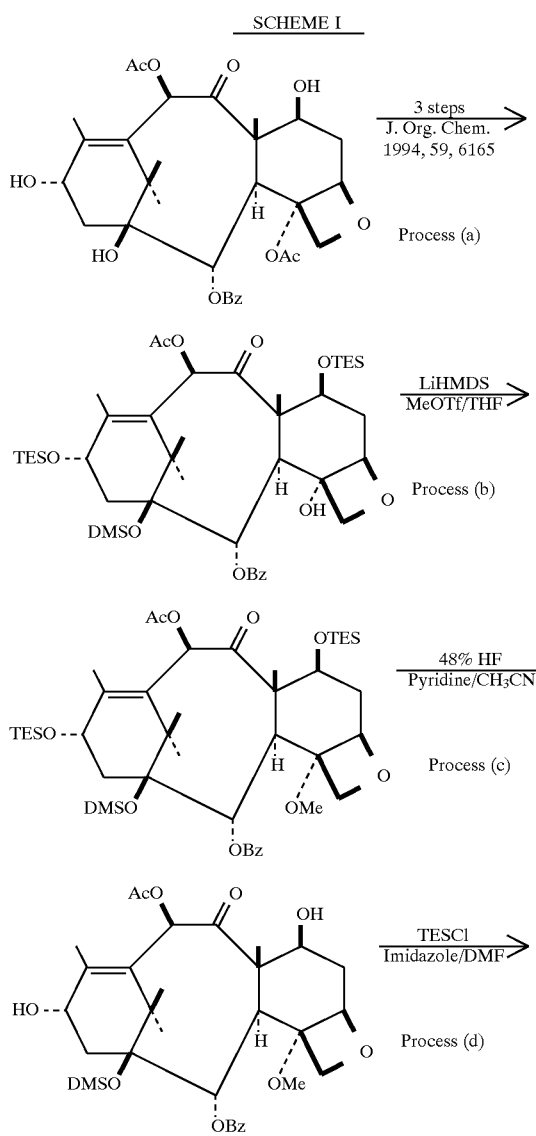

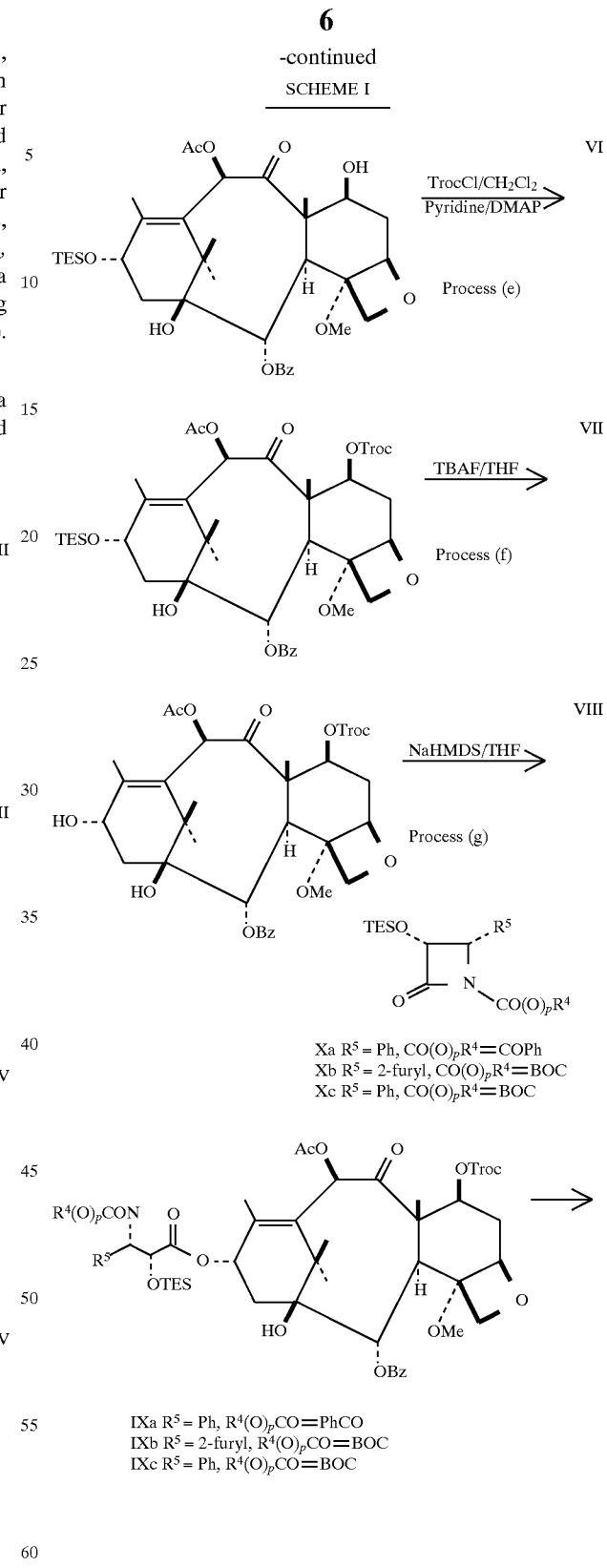

SCHEME I -continued

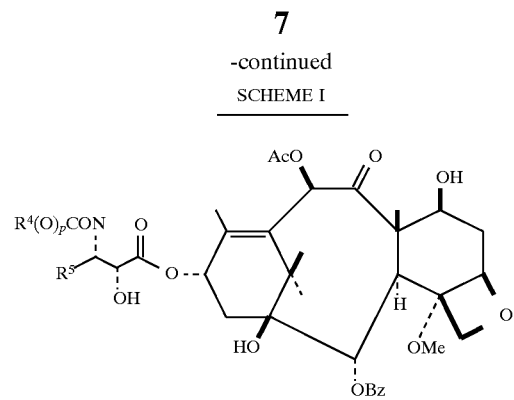

Ia R⁵ = Ph, R⁴(O)$_p$CO=PhCO
Ib R⁵ = 2-furyl, R⁴(O)$_p$CO=BOC
Ic R⁵ = Ph, R⁴(O)$_p$CO=BOC

SCHEME II

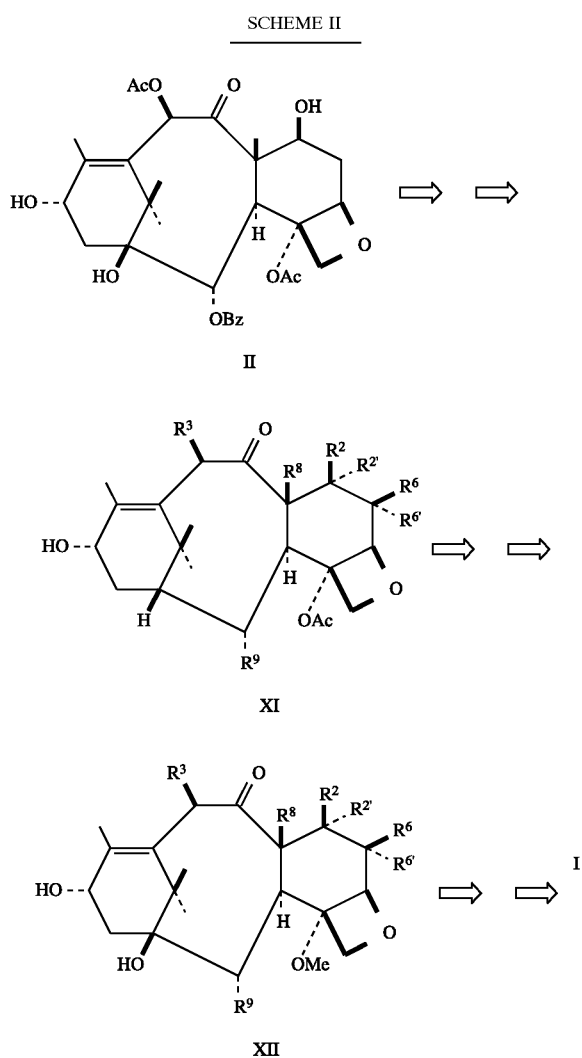

SCHEME III

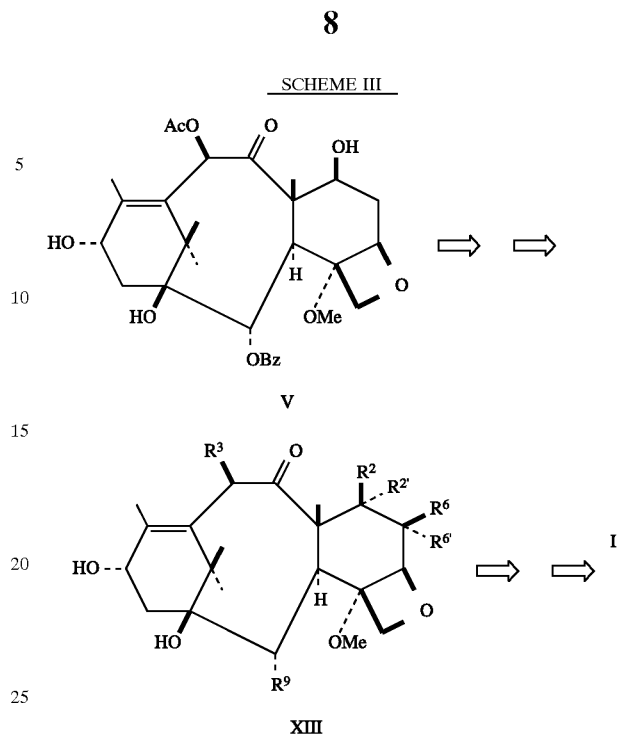

DESCRIPTION OF SPECIFIC EMBODIMENTS

The specific examples that follow illustrate the syntheses of the compound of the instant invention, and is not to be construed as limiting the invention in sphere or scope. The method may be adapted to variations in order to produce the compound embraced by this invention but not specifically disclosed. Further, variations of the methods to produce the same compound in somewhat different manner will also be evident to one skilled in the art.

In the following experimental procedures, all temperatures are understood to be in Centigrade (C) when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs or br s), broad doublet (bd or br d), broad triplet (bt or br t), broad quartet (bq or br q), singlet (s), multiplet (m), doublet (d), quartet (q), triplet (t), doublet of doublet (dd), doublet of triplet (dt), and doublet of quartet (dq). The solvents employed for taking NMR spectra are acetone-d$_6$ (deuterated acetone). DMSO-d$_6$ (perdeuterodimethylsulfoxide), D$_2$O (deuterated water), CDCl$_3$ (deuterochloroform) and other conventional deuterated solvents. The infrared (IR) spectral description include only absorption wave numbers (cm$^{-1}$) having functional group identification value.

Celite is a registered trademark of the Johns-Manville Products Corporation for diatomaceous earth.

The abbreviations used herein are conventional abbreviations widely employed in the art. Some of which are: DAB (deacetylbaccatin III); MS (mass spectrometry); HRMS (high resolution mass spectrometry); Ac (acetyl); Ph (phenyl); v/v (volume/volume); FAB (fast atom bombardment); NOBA (m-nitrobenzyl alcohol); min minute (s)); h or hr(s) (hour(s)); BOC (t-butoxycarbonyl); CBZ or Cbz (benzyloxycarbonyl); Bn (benzyl); Bz (benzoyl); Troc (2,2,2-richloroethyloxycarbonyl), DMS (dimethylsilyl), TBAF (tetrabutylammonium fluoride), DMAP (4-dimethylaminopyridine); TES (triethylsilyl); DMSO (dimethylsulfoxide); THF (tetrahydrofuran); HMDS (hexamethyldisilazane); MeOTf (methyltriflate).

Preparation of compound IV:

A THF solution (12 mL) of 4-deacetyl baccatin III of formula III (500 mg, 0.602 mmol) was treated at 0° C. with LiHMDS (0.723 mL, 1M, 0.723 mmol) for 20 mins. Methyltriflate (88.5 µL, 0.783 mmol) was then added and the reaction mixture was maintained at 0° C. for 60 mins. At this point, the reaction was quenched with saturated $NH_4Cl$ (5 mL). The reaction mixture was extracted with EtOAc (100 mL) and washed with water and brine. The organic layer was dried ($MgSO_4$) and concentrated in vacuo. The residue was purified with silica gel chromatography (10% EtOAc/Hexanes) to provide 371 mg (73%) of the desired C4 methyl ether derivative IV.

$^1$H NMR (300 MHz, $CDCl_3$): δ 8.07-8.04 (m, 2H), 7.54-7.40 (m, 3H), 6.41 (s, 1H), 5.65 (d, J=6.2 Hz, 1H), 4.95 (m, 2H), 4.55 (m, 1H), 4.21 (AB q, J=8.5 Hz, 2H), 3.91 (dd, J=6.1 Hz, J'=11.6 Hz, 1H), 3.44 (s, 3H), 3.35 (d, J=6.1 Hz, 1H), 2.85 (m, 1H), 2.36 (m, 2H), 2.16 (s, 3H), 2.12 (s, 3H), 1.96 (m, 1H), 1.62 (s, 3H), 1.18 (s, 3H), 1.06-0.50 (m, 30H), 0.03 (d, J=2.7 Hz, 3H), −0.30 (d, J=2.7 Hz, 3H).

HRMS calcd. for $C_{44}H_{72}O_{10}Si_3Na(MNa+)$=867.4331, found: 867.4308.

Preparation of compound V:

A $CH_3CN$ solution (7.5 mL) of IV (371 mg, 0.440 mmol) was treated successively with pyridine (1.30 mL) and 48% HF (4.0 mL) at 0° C. The reaction was stirred at 0° C. for 1 hr, and then kept at 5° C. for 12 hr. The reaction mixture was diluted with EtOAc (100 mL) and washed with 1N HCl (10 mL), followed by saturated $NaHCO_3$ (4×20 mL) and water. The organic layer was dried and concentrated in vacuo. The residue was chromatographed (70% EtOAc/Hexanes) to afford 217 mg (89%) of the C4 methyl ether baccatin III of formula V.

$^1$H NMR (300 MHz, $CDCl_3$): δ 8.00-7.98 (m, 2H), 7.61-7.43 (m, 3H), 6.28 (s, 1H), 5.55 (d, J=5.8 Hz, 1H), 4.98 (m, 1H), 4.51 (t, 1H), 4.37 (AB q, J=9.5 Hz, 2H), 3.97 (m, 1H), 3.63 (s, 3H), 3.52 (d, J=5.9 Hz, 1H), 3.27 (d, J=11.0 Hz, 1H), 2.61-1.03 (m, 19H, incl. singlets at 2.23, 2.05, 1.59, 1.07, 1.03, 3H each).

Preparation of compound VI:

To a DMF solution (4 mL) of V (114 mg, 0.204 mmol) was added imidazole (55 mg, 0.816 mmol) and TESCl (137 µL, 0.816 mmol) at 0° C. The reaction was allowed to stir at that temperature for 45 min. At this point, the reaction was quenched with saturated $NH_4Cl$ (4 mL) and diluted with EtOAc (60 mL). The organic layer was washed with water (4×7.5 mL) and brine (5 mL). The resulting organic layer was dried ($MgSO_4$) and concentrated in vacuo. The residue was chromatographed (20–40–80% EtOAc/Hexanes) to provide 73 mg (53%) of the C13 mono-silylated product VI as the major product, along with 26 mg (23%) of the recovered starting material V and small amounts of the C7,13-bis-silylated baccatin III as a minor product.

$^1$H NMR (300 MHz, $CDCl_3$) of VI: δ 8.06–8.03 (m, 2H), 7.59–7.41 (m, 3H), 6.26 (s, 1H), 5.58 (d, J=6.5 Hz, 1H), 5.02-4.91 (m, 2H), 4.21 (AB q, J=8.3 Hz, 2H), 3.90 (m, 1H), 3.42 (s, 3H), 3.35 (d, J=6.4 Hz, 1H), 2.77-1.10 (m, 20H, incl. singlets at 2.24, 2.03, 1.65, 1.15, 1.10, 3H each), 1.02 (m, 9H), 0.67 (m, 6H).

HRMS calcd. for $C_{36}H_{52}O_{10}SiNa(MNa+)$=695.3228, found: 695.3212.

Preparation of compound VII:

C13 monosilylated baccatin derivative VI (115 mg, 0.171 mmol) was dissolved in $CH_2Cl_2$ (1.5 mL). To this solution at room temperature was added pyridine (50 µL) and TrocCl (50 µL). A catalytic amount of DMAP was also added. After stirring at room temperature for 1.5 hr, the solvent was removed and the residue was purified with silica gel chromatography (20% EtOAc/Hexanes) to afford 137 mg (94%) of the desired C7 Troc-protected baccatin III of formula VII.

$^1$H NMR (300 MHz, $CDCl_3$): δ 8.05-8.02 (m, 2H), 7.60-7.42 (m, 3H), 6.32 (s, 1H), 5.58 (d, J=6.3 Hz, 1H), 5.04 (m, 2H), 4.92 (d, J=7.8 Hz, 1H), 4.85 (s, 1H), 4.62 (d, J=11.9 Hz, 1H), 4.22 (AB q, J=8.4 Hz, 2H), 3.50 (d, J=6.3 Hz, 1H), 3.46 (s, 3H), 2.77 (dd, J=7.2 Hz, J'=15.2 Hz, 1H), 2.47 (m, 1H), 2.16-0.63 (m, 32H, incl. singlets at 2.16, 2.09, 1.77, 3H each, 1.12, 6H).

HRMS calcd. for $C_{39}H_{53}SiO_{12}Cl_3Na(MNa+)$=869.2270, found: 869.2261.

Preparation of compound VIII:

A THF solution (3 mL) of VII (137 mg, 0.162 mmol) was treated at −10° C. with TBAF (0.324 mL, 1M, 0.324 mmol). After stirring 1.5 hr at that temperature, the solvent was removed and the residue was chromatographed (40–60% EtOAc/Hexanes) to afford 110 mg (93%) of the desired product VIII.

$^1$H NMR (300 MHz, $CDCl_3$): δ 8.00-7.97 (m, 2H), 7.62-7.44 (m, 3H), 6.32 (s, 1H), 5.56 (d, J=5.9 Hz, 1H), 5.12 (dd, J=6.4 Hz, J'=12.0 Hz, 1H), 5.04 (m, 2H), 4.61 (d, J=12.0 Hz, 1H), 4.51 (t, 1H), 4.34 (AB q, J=9.6 Hz, 2H), 3.67 (d, J=5.9 Hz, 1H), 3.64 (s, 3H), 3.19 (d, J=10.9 Hz, 1H), 2.59-1.02 (m, 19H, including singlets at 2.16, 2.12, 1.74, 1.10, 1.02, 3H each).

HRMS calcd. for VIII $C_{33}H_{39}O_{12}Cl_3Na(MNa+)$= 755.1405, found: 755.1379.

Preparation of compound IXa:

A THF solution (4 mL) of VIII (175 mg, 0.239 mmol) was treated at −40° C. with NaHMDS (0.286 mL, 1M, 0.286 mmol), followed immediately by a THF solution (1 mL) of β-lactam Xa (128 mg, 0.335 mmol). The reaction mixture was warmed to 0° C. and stirred for 100 mins. At this point, the reaction was quenched with saturated $NH_4Cl$ (5 mL) and extracted with EtOAc (100 mL). The organic layer was washed with water and brine and then dried with $MgSO_4$. Evaporation of the solvent and silica gel chromatography (20–30–60% EtOAc/Hexanes) of the resulting residue thus provided 122 mg (46%) of the desired product IXa, along with 60 mg (34%) of the recovered VIII.

$^1$H NMR (300 MHz, $CDCl_3$): δ 8.13-7.18 (m, 16H), 6.34 (s, 1H), 6.26 (t, J=8.1 Hz, 1H), 5.82 (d, J=8.7 Hz, 1H), 5.61 (d, J=6.3 Hz, 1H), 5.16 (m, 2H), 5.05 (d, J=12.0 Hz, 1H), 4.71 (d, J=1.7 Hz, 1H), 4.64 (d, J=12.0 Hz, 1H), 4.34 (AB q, J=9.2 Hz, 2H), 3.71 (s, 3H), 3.43 (d, J=5.1 Hz, 1H), 3.09 (dd, J=7.2 Hz, J'=15.4 Hz, 1H), 2.51 (m, 1H), 2.23-0.31 (m, 32H, incl. singlets at 2.17, 2.05, 1.83, 1.165, 1.255, 3H each).

HRMS calcd. for $C_{55}H_{66}NSiO_{15}Cl_3Na(MNa+)$= 1136.3165, found: 1136.3149.

Preparation of 4-deacetyloxy-4-methoxypaclitaxel (Ia):

To a THF solution (2 mL) of IXa (100 mg, 0.090 mmol) was added TBAF (135 uL, 1M, 0.135 mmol) at 0° C. The reaction went to completion in 1 hr. The solvent was then removed and the residue was chromatographed (40–50%

EtOAc/Hexanes) to provide 84 mg (94%) of the corresponding C2' desilylated intermediate. A part of this material (78 mg, 0.078 mmol) was then dissolved in MeOH (0.7 mL) and AcOH (0.7 mL). To this solution was added a large excess of the acid washed Zn (76 mg, 1.170 mmol). The reaction mixture was heated at 45° C. for 1 hr. At this point, the solvent was partially removed, and the resulting residue was purified with silica gel chromatography (60–80% EtOAc/Hexanes) to give 61 mg (95%) of the final C4 methyl ether carrying paclitaxel derivative of formula Ia.

$^1$H NMR (300 MHz, CDCl$_3$): δ 8.15-7.34 (m, 15H), 7.12 (d, J=9.1 Hz, 1H), 6.25 (s, 1H), 6.22 (m, 1H), 5.90 (d, J=8.9 Hz, 1H), 5.60 (d, J=6.2 Hz, 1H), 5.04 (dd, J=3.2 Hz, J'=9.7 Hz, 1H), 4.80 (d, J=1.8 Hz, 1H), 4.30 (AB q, J=9.1 Hz, 2H), 3.90 (dd, J=5.9 Hz, J'=11.8 Hz, 1H), 3.65 (s, 3H), 3.26 (d, J=6.2 Hz, 1H), 3.09 (dd, J=7.0 Hz, J'=15.4 Hz, 1H), 2.44 (m, 1H), 2.23-1.12 (m, 17H, including singlets at 2.23, 1.85, 1.65, 1.16, 1.12, 3H each).

$^{13}$C NMR (75 MHz, CDCl$_3$): δ 204.1, 172.1, 171.1, 167.1, 166.7, 140.8, 138.5, 134.5, 134.0, 133.4, 131.7, 130.1, 129.3, 128.8, 128.6, 128.5, 128.0, 126.9, 126.8, 81.4, 79.7, 78.3, 75.7, 74.9, 73.5, 73.4, 72.5, 72.1, 58.2, 54.7, 50.0, 48.8, 42.9, 35.3, 34.8, 26.8, 20.8, 20.6, 15.5, 9.9.

HRMS calcd. for C$_{46}$H$_{51}$NO$_{13}$Na(MNa+)=848.3258, found: 848.3227.

Preparation of compound IXb:

A THF solution (2.7 mL) of VIII (98 mg, 0.134 mmol) was treated with NaHMDS (0.174 mL, 1M, 0.174 mmol) at −40° C., followed by β-lactam Xb (74 mg, 0.201 mmol). The reaction was stirred at −20° C. for 40 min and then quenched with saturated NH$_4$Cl (3 mL). The reaction mixture was then extracted with EtOAc (50 mL). The organic layer was washed with water and brine and dried (MgSO$_4$). Evaporation of the solvent and the purification of the residue thus provided 100 mg (68%) of the desired product IXb.

$^1$H NMR (300 MHz, CDCl$_3$): δ 8.11-8.09 (m, 2H), 7.55-7.42 (m, 4H), 6.38-6.27 (m, 4H), 5.61 (d, J=6.1 Hz, 1H), 5.41 (m, 2H), 5.11 (m, 2H), 5.02 (d, J=12.2 Hz, 1H), 4.78 (s, 1H), 4.62 (d, J=12.0 Hz, 1H), 4.29 (AB q, J=9.1 Hz, 2H), 3.61 (s, 3H), 3.43 (d, J=6.0 Hz, 1H), 3.11 (dd, J=6.8 Hz, J'=15.5 Hz, 1H), 2.50 (m, 1H), 2.20–0.40 (m, 41H, including singlets at 2.17, 2.01, 1.80, 1.18, 1.16, 3H each, 1.41, 9H).

HRMS calcd. for C$_{51}$H$_{68}$NO$_{17}$Cl$_3$SiNa(MNa+)= 1122.3220, found: 1122.3247.

Preparation of 4-deacetyloxy-4-methoxy-3'-desphenyl-3'-(2-furyl)-3'-N-debenzoyl-3'-N-butoxycarbonyl(paclitaxel) (Ib):

A THF solution (2 mL) of IX)b (94 mg, 0.0855 mmol) was treated at −5° C. with TBAF (0.171 mL, 1M, 0.171 mmol) for 1 hr. The solvent was then removed, and the residue was chromatographed (40% EtOAc/Hexanes) to give 79 mg (94%) of the desired C2' desilylated intermediate. A part of this material (49 mg, 0.050 mmol) was dissolved in MeOH (0.5 mL) and AcOH (0.5 mL). To this mixture was added acid washed Zn (49 mg, 0.746 mmol). The resulting slurry was heated at 45° C. for 1 hr. The solvent was partially removed and the residue was chromatographed (40–80% EtOAc/Hexanes) to provide 41 mg (100%) of the desired C4 methyl ether paclitaxel analog Ib.

$^1$H NMR (300 MHz, CDCl$_3$): δ 8.10-8.07 (m, 2H), 7.60-7.44 (m, 4H), 6.41-6.36 (m, 2H), 6.28 (m, 2H), 5.62 (d, J=6.1 Hz, 1H), 5.38 (m, 2H), 5.05 (dd, J=3.3 Hz, J'=9.8 Hz, 1H), 4.73 (s, 1H), 4.29 (AB q, J=9.2 Hz, 2H), 3.92 (m, 1H), 3.56 (s, 3H), 3.26 (d, J=6.1 Hz, 1H), 3.08 (dd, J=6.9 Hz, J'=15.3 Hz, 1H), 2.44 (m, 1H), 2.25-1.15 (m, 26H, incl. singlets at 2.25, 1.93, 1.65, 1.21, 1.15, 3H each, 1.41, 9H).

$^{13}$C NMR (75 MHz, CDCl$_3$): δ 204.0, 171.9, 171.1, 167.0, 154.8, 151.6, 142.2, 141.0, 134.4, 133.4, 129.9, 129.3, 128.6, 110.5, 107.6, 81.3, 80.0, 79.8, 79.2, 75.7, 74.7, 73.6, 72.5, 72.1, 71.7, 58.3, 51.1, 49.7, 48.9, 43.0, 35.3, 34.7, 28.2, 26.8, 20.7, 20.4, 15.6, 9.8.

HRMS calcd. for C$_{42}$H$_{53}$NO$_{15}$Na(MNa+)=834.3313, found: 834.3332.

Similarly, compound of formula IXc and 4-deacetyloxy-4-methoxy-3'-N-debenzoyl-3'-N-butoxycarbonyl (paclitaxel) (Ic) were also prepared.

$^1$H NMR (300 MHz, CDCl3) of IXc: δ: 8.11-8.08 (m, 2H), 7.57-7.30 (m, 8H), 6.31 (m, 2H), 5.60 (m, 2H), 5.42 (d, J=9.6 Hz, 1H), 4.84 (AB q, J=12.0 Hz, 2H), 4.57 (s, 1H), 4.32 (AB q, J=9.2 Hz, 2H), 3.69 (s, 3H), 3.46 (d, J=5.9 Hz, 1H), 3.14 (dd, J=7.0 Hz, J'=15.4 Hz, 1H), 2.60-1.17 (m, 27H, incl. singlets at 2.17, 2.03, 1.81, 1.20, 1.18, 3H each, 1.39, 9H), 0.76 (m, 9H), 0.38 (m, 6H).

HRMS calcd. for C$_{53}$H$_{70}$NO$_{16}$Cl$_3$SiNa(MNa+)= 1132.3427, found: 1132.3380.

$^1$H NMR (300 MHz, CDCl3) of Ic: δ: 8.10-8.07 (m, 2H), 7.60-7.33 (m, 8H), 6.25 (m, 2H), 5.62 (d, J=6.1 Hz, 1H), 5.50 (d, J=9.7 Hz, 1H), 5.39 (d, J=9.4 Hz, 1H), 5.06 (dd, J=3.3 Hz, J'=9.7 Hz, 1H), 4.65 (s, 1H), 4.30 (AB q, J=9.2 Hz, 2H), 3.93 (dd, J=6.0 Hz, J'=11.9 Hz, 1H), 3.63 (s, 3H), 3.27 (d, J=6.1 Hz, 1H), 3.07 (dd, J=6.7 Hz, J'=15.8 Hz, 1H), 2.50-1.15 (m, 27H, incl. singlets at 2.25, 1.87, 1.65, 1.21, 1.15, 3H each, 1.39, 9H).

$^{13}$C NMR (75 MHz, CDCl$_3$) of Ic: δ: 204.0, 172.1, 171.1, 167.1, 154.9, 141.0, 138.9, 134.5, 133.4, 129.9, 129.3, 128.7, 128.6, 127.6, 126.5, 81.3, 79.8, 78.2, 75.7, 74.7, 73.9, 73.6, 72.5, 72.0, 58.3, 55.8, 49.9, 48.8, 43.0, 35.3, 34.7, 28.2, 26.9, 20.7, 20.4, 15.6, 9.8.

HRMS calcd. for C$_{44}$H$_{55}$NO$_{14}$Na(MNa+)=844.3520, found: 844.3509.

In vitro cytotoxicity study

Cytotoxicity was assessed in HCT-116 human colon carcinoma cells by XTT (2,3-bis(2-methoxy-4-nitro-5-sulfphenyl)-5-[(phenylamino)carbonyl]2H-tetrazolium hydroxide) assay as reported in D. A. Scudiero, et al., "Evaluation of soluble tetrazolium/formazan assay for cell growth and drug sensitivity in culture using human and other tumor cell lines," *Cancer Res.* 48:4827–4833, 1988. Cells were plated at 4000 cells/well in 96 well microtiter plates and 24 hours later drugs were added and serial diluted. The cells were incubated at 37° C. for 72 hours at which time the tetrazolium dye, XTT, was added. A dehydrogenase enzyme in live cells reduces the XTT to a form that absorbs light at 450 nm which can be quantitated spectrophotometrically. The greater the absorbance, the greater the number of live cells. The results are expressed in Table I as an IC$_{50}$, which is the drug concentration required to inhibit cell proliferation (i.e., absorbance at 450 nm) to 50% of that of untreated control cells.

TABLE I

In vitro cytotoxicity data against human colon carcinoma cells.

| Compound | IC$_{50}$ (nM) HCT-116 | Ratio of IC$_{50}$ of Compound I over Paclitaxel |
|---|---|---|
| Paclitaxel | 1.3–2.3 | — |
| Compound Ia | 34.7 | 21.7 |
| Compound Ib | 3.7 | 1.61 |
| Compound Ic | 2.2 | 1.69 |

The compound of formula I of the instant invention is an effective tumor inhibiting agent, and is useful in human and/or veterinary medicine. Thus, another aspect of the instant invention concerns a method for inhibiting human and/or other mammalian tumors which comprises administering to a tumor bearing host an antitumor effective amount of compound of formula I.

For treating a variety of tumors, the compound of formula I of the present invention may be used in a manner similar to that of paclitaxel, e.g. see Physician's Desk Reference, 49th Edition, Medical Economics, p 682,1995. The dosage, mode and schedule of administration for the compound of this invention are not particularly restricted; an oncologist skilled in the art of cancer treatment will be able to ascertain, without undue experimentation, an appropriate treatment protocol for administering the compound of the present invention. Thus the compound of formula I may be administered via any suitable route of administration, preferably parenterally. Parenteral administration includes intravenous, intraperitoneal, intramuscular, and subcutaneous administration . Intraperitoneal or intravenous administration is particularly preferred.

The doses utilized to implement the methods in accordance with the invention are the ones that make it possible to administer prophylactic treatment or to evoke a maximal therapeutic response. The doses vary, depending on the type of administration, the particular product selected, and the personal characteristics of the subject to be treated. In general, the doses are the ones that are therapeutically effective for the treatment of disorders caused by abnormal cell proliferation. The products in accordance with the invention can be administered as often as necessary in order to obtain the desired therapeutic effect. Some patients may respond rapidly to relatively high or low doses, and then require mild maintenance or no maintenance dose at all. The dosage may be, for example, in the range of about 20 to about 500 mg/m$^2$ over 1 to 100 hours. The actual dose used will vary according to the particular composition formulated, the route of administration, and the particular site, host and type of tumor being treated. Many factors that modify the action of the drug will be taken into account in determining the dosage including age, weight, sex, diet and the physical condition of the patient.

The present invention also provides pharmaceutical formulations (compositions) containing an antitumor effective amount of compound of formula I in combination with one or more pharmaceutically acceptable carriers, excipients, diluents or adjuvants. The formulations can be prepared in accordance with conventional methods. Examples of formulating paclitaxel or derivatives thereof may be found in, for example, U.S. Pat. Nos. 4,960,790 and 4,814,470, and such examples may be followed to formulate the compound of this invention. For example, compound of formula I may be formulated in the form of tablets, pills, powder mixtures, capsules, injectables, solutions, suppositories, emulsions, dispersions, food premix, and in other suitable forms. It may also be manufactured in the form of sterile solid compositions, for example, freeze dried and, if desired, combined with other pharmaceutically acceptable excipients. Such solid compositions can be reconstituted with sterile water, physiological saline, or a mixture of water and an organic solvent, such as propylene glycol, ethanol, and the like, or some other sterile injectable medium immediately before use for parenteral administration.

Typical of pharmaceutically acceptable carriers are, for example, manitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

What is claimed is:

1. A compound of formula I

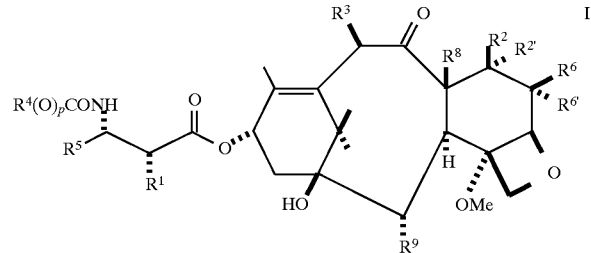

wherein $R^1$ is hydroxy; $R^2$ is hydroxy; $R^{2'}$ is hydrogen; $R^{6'}$ is hydrogen; $R^3$ is acetyloxy; $R^8$ is methyl; $R^6$ is hydrogen; $R^9$ is benzyloxy; $R^4$ and $R^5$ are independently $C_{1-6}$ alkyl, $C_{2-6}$ alkenyl, $C_{2-6}$ alkynyl, or —Z—$R^{10}$; Z is a direct bond, $C_{1-6}$ alkyl or $C_{2-6}$ alkenyl; $R^{10}$ is aryl, substituted aryl, $C_{3-6}$ cycloalkyl or heteroaryl; and p is 0 or 1.

2. The compound of claim 1 that is 4-deacetyloxy-4-methoxypaclitaxel.

3. The compound of claim 1 that is 4-deacetyloxy-4-methoxy-3'-desphenyl-3'-(2-furyl)-3'-N-debenzoyl-3'-N-butoxycarbonyl(paclitaxel).

4. The compound of claim 1 that is 4-deacetyloxy-4-methoxy-3'-N-debenzoyl-3'-N-butoxycarbonyl(paclitaxel).

* * * * *